United States Patent [19]

Fernwood et al.

[11] Patent Number: 5,984,677
[45] Date of Patent: Nov. 16, 1999

[54] AIR ABRASIVE PARTICLE APPARATUS

[75] Inventors: Mark S. Fernwood; Thomas S. Blake; Craig R. Bruns, all of Danville, Calif.

[73] Assignee: Danville Engineering, San Ramon, Calif.

[21] Appl. No.: 08/952,291

[22] PCT Filed: May 9, 1996

[86] PCT No.: PCT/US96/06676

§ 371 Date: Feb. 17, 1998

§ 102(e) Date: Feb. 17, 1998

[87] PCT Pub. No.: WO96/35390

PCT Pub. Date: Nov. 14, 1996

[51] Int. Cl.⁶ .................................................. A61C 3/02
[52] U.S. Cl. .............................................. 433/88; 451/90
[58] Field of Search .................................. 433/88; 451/6, 451/75, 90, 91, 99; 239/144, 311, 317, 74; 222/161, 196

[56] References Cited

U.S. PATENT DOCUMENTS

| | | |
|---|---|---|
| 2,661,537 | 12/1953 | Angell . |
| 2,696,049 | 12/1954 | Black . |
| 2,738,234 | 3/1956 | Anderson . |
| 2,759,266 | 8/1956 | Cassani . |
| 2,814,877 | 12/1957 | Tilden . |
| 3,139,705 | 7/1964 | Histed . |
| 3,149,759 | 9/1964 | Manley . |
| 3,344,524 | 10/1967 | Kulischenko . |
| 3,534,503 | 10/1970 | Kulischenko . |
| 3,631,631 | 1/1972 | Greenstein . |
| 3,852,918 | 12/1974 | Black . |
| 3,882,638 | 5/1975 | Black . |
| 3,920,155 | 11/1975 | Whited . |
| 4,067,150 | 1/1978 | Merrigan . |
| 4,482,322 | 11/1984 | Hain et al. . |
| 4,487,582 | 12/1984 | Warrin . |
| 4,494,932 | 1/1985 | Rzewinski . |
| 4,522,237 | 6/1985 | Endo et al. . |
| 4,708,534 | 11/1987 | Gallant . |
| 4,733,503 | 3/1988 | Gallant . |
| 5,178,496 | 1/1993 | Trieb et al. . |
| 5,330,354 | 7/1994 | Gallant . |
| 5,350,299 | 9/1994 | Gallant . |
| 5,525,058 | 6/1996 | Gallant et al. ............................. 433/88 |

FOREIGN PATENT DOCUMENTS

PCT/US93/02939  3/1993  WIPO .

OTHER PUBLICATIONS

Buonocore, M.G., "A Simple Method of Increasing the Adhesion of Acrylic Filling Materials to Enamel Surfaces," Journal of Dental Research, 34(6):849–853 (1955).

Malcom, J.A., "The Airbrasive Technique," A Manual, pp. 4–54 (1953).

S.S. White Dental Mfg. Co., The S. S. White 'Airdent' Unit, Directions for its Operation, Maintenace, Care, pp. 5–8.

*Primary Examiner*—Nicholas D. Lucchesi
*Attorney, Agent, or Firm*—Cooley Godward LLP

[57] ABSTRACT

This invention is a method and apparatus for an air abrasive unit such as those used in the dental field. This method and apparatus utilizes an internal vibrator motor with vibration transmitters which transmit the vibration throughout the abrasive jar. The abrasive pickup assembly uses pressure differentials to suck up abrasive through a screen which controls the flow rate and particle size of the abrasive flowing through the system. The system can utilize a photo-optical detection system to detect the abrasive level. Alternatively, a pressure/pulse detection system may be used to measure abrasive level. Dilution of the air/abrasive mixture and "air only" modes are possible with the present system. Depressurization and mere reductions of pressure can also be accommodated. The invention also includes a system for easily modifying the content of an air abrasive stream exiting the mixing chamber.

10 Claims, 10 Drawing Sheets

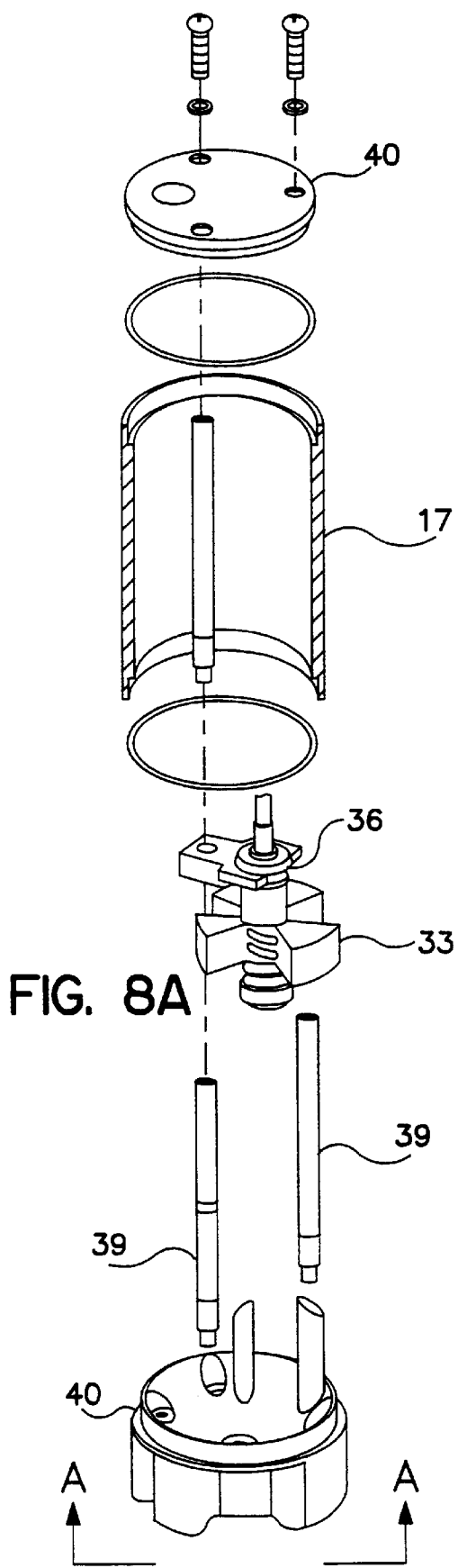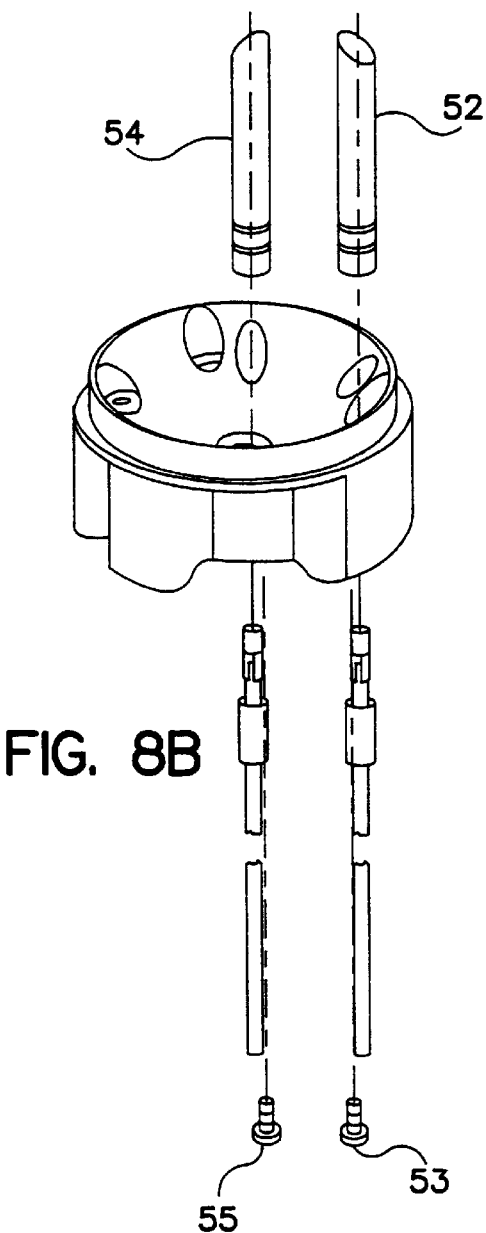
FIG. 8A
FIG. 8B

AIR ABRASIVE PARTICLE APPARATUS

INTRODUCTION

1. Technical Field

This invention relates to air abrasive technology. More particularly, it relates to methods and apparati for supplying abrasive particles to abrade a surface. The invention is particularly useful for dental applications.

2. Background

The use of air abrasive in the dental industry has considerably reduced the pain and general unpleasantness involved in dental procedures. Traditional air abrasive delivery systems worked much like a salt shaker. They were basically chambers which would be vibrated in order to force the abrasive out of the holes at the bottom of the chamber. Another type of air abrasive delivery system vibrated the abrasive to flow up through a circular track to bring sand up through the top of the chamber. These systems had the common problem of excessive noise and vibration. Systems can be found which avoid the excessive noise and vibration by blowing air over the top of the abrasive to create a dust cloud which could be blown or sucked out to the end piece. These systems had severe difficulty with abrasive flow control.

In addition to the difficulties of obtaining predictable uniform mixing of air with abrasive particles, the existing air abrasive devices do not provide reliable, flexible means for modifying the content of abrasive stream exiting the nozzle from the dental handpiece. The invention set forth in its various aspects in this specification solve these problems.

3. Objects of the Invention

An object of this invention is to provide a device that is useful for more efficiently mixing abrasive particles with air to create a pressurized, moving air/abrasive stream that is directed onto a surface to clean the surface or abrade it to give it a different appearance or to prepare it for further treatment.

Another object of this invention is to provide a device that is useful for efficiently mixing abrasive particles with air to create a pressurized, moving air/abrasive stream that is directed onto a tooth surface to clean the tooth surface or to abrade the surface in preparation for bonding or cavity work.

Another object of this invention is to provide a device or system for more efficiently cleaning or abrading a surface, particularly a tooth surface, which device or system has an easily adjustable flow rate of an air/abrasive stream without having to resort to using multiple flow paths to achieve such adjustable flow rate.

Another object of this invention is to provide a device or system that is simpler in design than similar, existing devices or systems for abrading a surface using an abrasive-laden air stream.

Another object of this invention is to provide an improved device or system for abrading a surface using an abrasive-laden air stream, wherein the improvement allows for the easy dilution of the abrasive particles in the air stream.

Other objects of this invention will be apparent to one of ordinary skill upon reading the specification and claims of this patent application.

SUMMARY OF THE INVENTION

One aspect of this invention is a device for producing a pressurized stream of a gas and suspended particles, which device comprises a chamber, an inlet tube for allowing particles from a particle source to flow to the chamber, the tube having a proximal end and a distal end, a separating means positioned near the distal end of the particle inlet line to prevent particles that are larger than the distal end opening of the inlet line from getting through the separating means, a gas inlet tube for allowing a gas to enter the chamber under pressure, said gas inlet tube having a proximal end and a distal end, and an outlet tube from said chamber for allowing a stream of fluidized particles to exit the chamber, wherein when the gas is forced through the gas inlet tube to enter the chamber and it flows across the proximal end of the particle inlet tube to create a low pressure region in the chamber which allows particles to flow through the separating means and the distal end of the particle inlet tube through the proximal end of the inlet tube and into the chamber where the particles are suspended within the chamber and forced out through the outlet tube under pressure in a stream of particles suspended in the gas.

Another aspect of this invention is a vibrator assembly that comprises a motor for producing vibrations in the assembly, a housing enclosing the motor, a vibration transmitting member attached to the housing and extending radially outward of the housing, a flexible collar extending around at least a portion of the housing, a bracket to fit around the collar and securely hold the collar and housing, and at the same time attach to a member to hold the assembly in place, wherein when the motor is provided with a source of power the assembly is caused to vibrate and the vibrations are transmitted away from the assembly through the vibration transmitting member.

Another aspect of this invention is a container suitable for holding a mass of flowable particles wherein said container is defined by top, bottom, and side walls, and positioned internally in the container is a vibrator assembly housing a motor which causes the internal vibrator assembly to vibrate, the internal vibrator assembly having at least one vibration transmitting member extending from the periphery of the assembly towards the sides of the container such that the vibrations of the assembly are distributed throughout the container so that when the container is filled with flowable particles the vibrational energy is distributed to the mass of the flowable particles such that as flowable particles are removed from the lower part of the container the level of the mass of flowable particulate material recedes at a relatively uniform rate with minimum cavitation occurring within the container.

Another aspect of this invention is a container defined by top, bottom, and side walls wherein said container is suitable for holding flowable particles within the container having a means for metering material out of said container from a lower portion of the container is located within the container, a vibrator assembly is located internal to said container and is designed to distribute vibrations throughout the mass of flowable particles so that the level of the flowable particulate material recedes at a relatively constant rate and an optical level sensing device is positioned within the container such that when the level of flowable particulate material drops below a predetermined level a signal is sent externally to indicate the level of the flowable particulate material within the container.

Another aspect of this invention is a dental air abrasive system comprising (a) a container, (b) a vibrator assembly positioned internally in the container, (c) a device for producing a pressurized stream of a gas and suspended particles located within the container and associated with the vibrator assembly, (d) a dental handpiece with a nozzle for directing a pressurized stream of gas/particles against a tooth surface, and (e) a transmission tube connecting the handpiece and pressurized stream of a gas and suspended particles.

Another aspect of this invention is a device for producing a pressurized stream of a gas and suspended abrasive particles, which device comprises (a) a source of a pressurized gas; (b) a source of abrasive particles; (c) a mixing means for combining the pressurized gas with said abrasive particles to produce the pressurized stream of gas and suspended particles; (d) an inlet line for the pressurized gas to flow to the mixing means; (e) an outlet line from the mixing means to carry the pressurized stream of gas and suspended particles away from the mixing means; (f) a variable pressure regulator means for controlling the pressure of the gas supplied to the mixing means through the inlet line; (g) a first mixing chamber positioned in the outlet line; (h) a source of regulated pressurized gas leading to the first mixing chamber to provide dilution of the pressurized stream of gas and suspended particles; (i) a nozzle means downstream of the first mixing chamber for delivering the pressurized stream of gas and suspended particles to a surface; and (j) a first valve located intermediate of the mixing means and nozzle means for regulating the flow of the pressurized stream of gas and suspended particles to the nozzle means so that the pressurized stream of gas and suspended particles may be directed against a surface to be abraded.

Another aspect of this invention is a device for producing a pressurized stream of a gas and suspended abrasive particles, which device comprises components (a)–(e) of the immediately preceding paragraph and (f) a pressure regulator means for providing a constant pressure of the gas supplied to the mixing means through the inlet line; (g) a first mixing chamber positioned in the outlet line; (h) a source of pressurized gas having the pressure regulated by a pulsed-duty cycle regulator and leading to the first mixing chamber to provide dilution of the pressurized stream of gas and suspended particles; (i) a nozzle means downstream of the first mixing chamber for delivering the pressurized stream of gas and suspended particles to a surface; and (j) a first valve located intermediate of the mixing means and nozzle means for regulating the flow of the pressurized stream of gas and suspended particles to the nozzle means so that the pressurized stream of gas and suspended particles may be directed against a surface to be abraded.

Another aspect of this invention is a device for producing a pressurized stream of a gas and suspended abrasive particles, which device comprises components (a)–(e) of the immediately preceding paragraph and (f) a variable pressure regulator means for controlling the pressure of the gas supplied to the mixing means through the inlet line;(g) a first mixing chamber positioned in the outlet line; (h) a source of pressurized gas having the pressure regulated by a pulsed-duty cycle regulator and leading to the first mixing chamber to provide dilution of the pressurized stream of gas and suspended particles; (i) a nozzle means downstream of the first mixing chamber for delivering the pressurized stream of gas and suspended particles to a surface; and (j) a first valve located intermediate of the mixing means and nozzle means for regulating the flow of the pressurized stream of gas and suspended particles to the nozzle means so that the pressurized stream of gas and suspended particles may be directed against a surface to be abraded.

Still other aspects of this invention will be apparent to one of ordinary skill in the art by reading the following specifications and claims.

BRIEF DESCRIPTION OF THE DRAWINGS

FIG. 8A, 8C and 8D are exploded views of the assemblage generally shown in FIG. 1.

FIG. 8B is an exploded view of the LED and photodiode assembly of FIG. 8A.

DETAILED DESCRIPTION AND PRESENTLY PREFERRED EMBODIMENTS

A first aspect of this invention is a device that is useful in air abrasive products in which a pressurized stream of air laden with abrasive particles is forced against a surface to remove material that is coated on the surface. Such air abrasive products are used in the dental industry to prepare teeth surfaces for various applications, in the metal finishing industry to remove coatings from a metal surface prior to further coating, in the sand blasting industry to clean stone or ceramic surfaces prior to applying a protective coating or simply to clean the surface, and other industries for similar purposes. The dimensions of the working parts of the device will depend upon the purpose for which it will be used and the industry in which it will be used. While the device will be described primarily in terms that are suitable for dental applications, it is to be understood that the device can be modified to be used in other industries. Also, while the device may be described herein primarily in combination with certain other components useful in the dental industry, it is to be understood that the device may be considered as an independent unit that can be used as a replacement part for an existing air abrasive unit that may need to be upgraded to improve or modify its performance characteristics.

In a broad description the device is for delivering a pressurized stream of gas and suspended particles, which device comprises a chamber;

an inlet tube for allowing particles from a particle source to flow to the chamber, the tube having a proximal end and a distal end;

a separating means positioned near the distal end of the particle inlet line to prevent particles that are larger than the distal end opening of the inlet line from getting through the separating means;

a gas inlet tube for allowing a gas to enter the chamber under pressure, the gas inlet tube having a proximal end and a distal end; and an outlet tube from said chamber for allowing a stream of fluidized particles to exit the chamber. When a pressurized gas is forced through the gas inlet tube line to enter the chamber and flow across the proximal end of the particle inlet tube, a low pressure region is created in the chamber which allows particles to flow through the separating means and the distal end of the particle inlet tube through the proximal end of the inlet tube and into the chamber where the particles are suspended within the chamber and forced out through the outlet tube under pressure in a stream of particles suspended in the gas.

Figure 1:
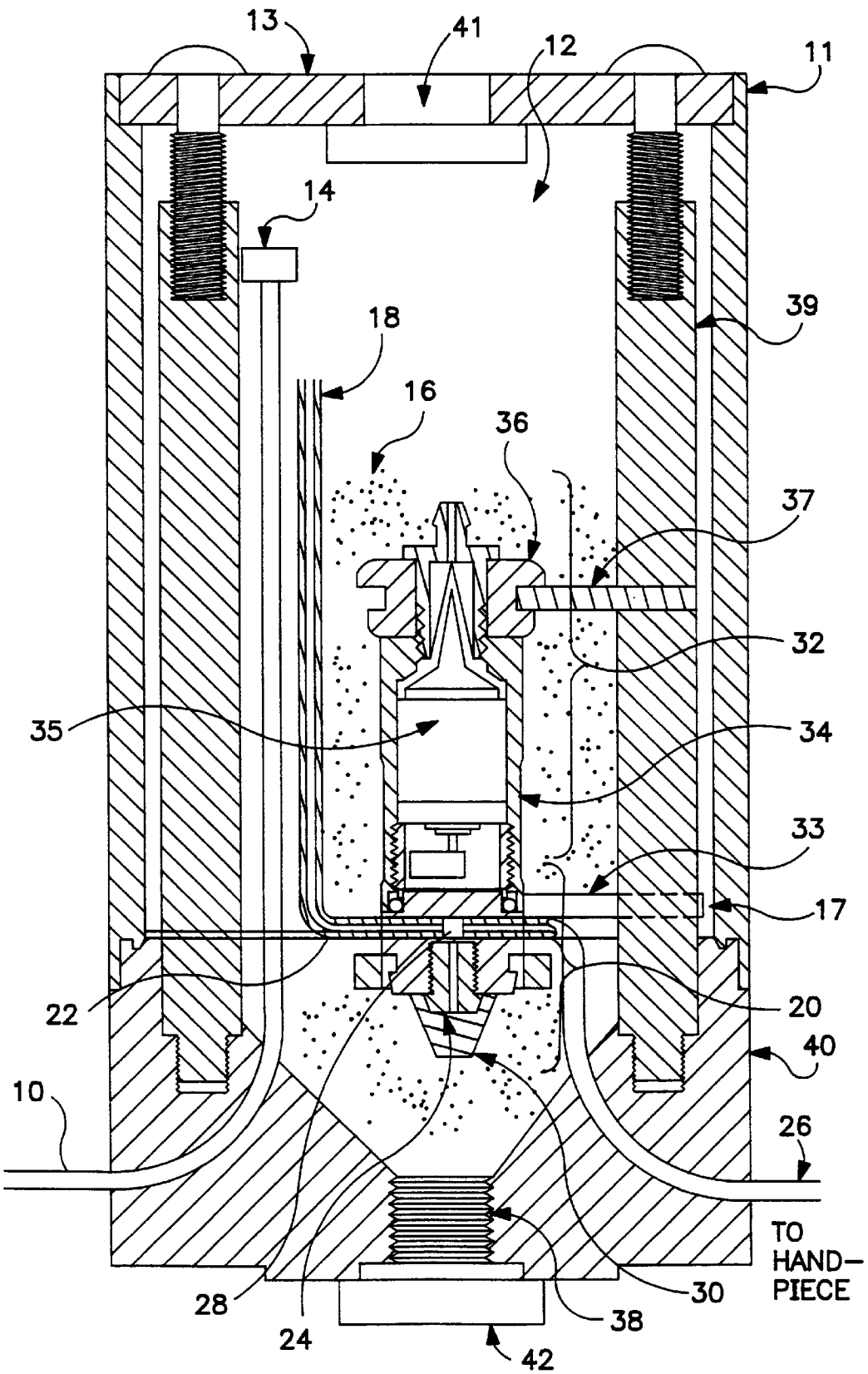
FIG. 1 is a vertical cross-sectional view of a combination of this invention comprising a container having positioned therein a vibrator assembly integrated with a device for producing a pressurized stream of gas and suspended particles.

FIG. 1 provides a view of the device in combination with various other components that, in combination with the device, form aspects of this invention. Broadly, the components are a pressurizable container in which flowable particles are held and in which the device is placed and a vibrating means that assists in ensuring a controlled flow of particles to the device. Turning to the details of FIG. 1, a compressed gas, such as air, flows through the pressurized air inlet 10 of jar or container 11, which is designed to be airtight and able to withstand high pressures. The pressurized gas flows through filter 14 and into the jar interior 12 that is defined by top wall 13, side walls 17 and bottom wall 40. The gas may be any suitable inert, dry gas that is used in the air abrasive industry such as carbon dioxide, nitrogen, air, and the like. Generally it is preferred that the gas is air and is dried to such an extent that it will not cause the particles to bind together as it enters the container. The gas will be pressurized to a level that is appropriate to the task at hand and may be anywhere from about 30 pounds per square inch (psi) to about 200 psi. For purposes in the dental industry the pressure will vary from about 40 psi to about 180 psi, preferably no more than 80 psi. The container interior 12 contains abrasive particles 16 and the pressurized air from the air inlet 10. The abrasive particles are of size and hardness ranges, flowability, and other characteristics that are appropriate for the purpose for which the air abrasive stream is to be used. For example, for dental purposes the particles should be of a size between about 20 microns to about 150 microns, preferably between about 25 to about 90 microns, and of a hardness of that of aluminum oxide (also referred to as alumina, commonly used for this purpose, see for example U.S. Pat. No. 2,696,049, which is incorporated herein by reference). For removal of paint, alumina or silica particles are suitable in a size range of up to 200 microns. For sandblasting stone or concrete surfaces, larger particles of up to 200 microns may be used.

The device for delivering a pressurized stream of a gas and suspended particles is shown generally as 20 in combination with a vibrator motor 32 to be discussed hereinafter. The pressurized gas of the jar interior 12 flows into the distal end 18 of gas inlet tube 22, which distal end 18 is positioned above the upper level 16 of the mass of flowable particles. Air flows from the distal end 18 of gas inlet tube 22 and into a chamber 28, where the gas and particles are mixed. Particles are allowed to enter chamber 28 through a particle inlet tube 24 that has a proximal end adjacent the particles 15. Between the distal end of the particle inlet tube 24 and the particles 15 is a separating or screening means 30 that acts to prevent or filter particles that might be larger than the distal end of the particle inlet tube from plugging the distal end or lodging in the tube. The flow of the pressurized gas from jar interior 12 across the proximal end of the particle inlet tube creates a low pressure in the pickup chamber 28 to cause the abrasive particles to flow through screen 30, into the pickup tube 24 and are suspended in pickup chamber 28 before being forced out the chamber through outlet tube 26.

The flow of abrasive particles through screen 30 not only prevents overly large particles from plugging up the system, but also acts as a flow restriction to regulate quantity of abrasive flow to the pickup tube 24. The abrasive flow into the pickup tube 24 can be regulated by selecting the inside diameter of inlet tube 24 and possibly by the length of the pickup tube 24. Once the abrasive particles 16 reach the pickup chamber 28, they mix with the pressurized air flowing from the inlet tube 22. The mixture of air/abrasive particles flows out of the outlet tube 26.

It is to be understood that cross-sectional design of tubes 22, 24 and 26 may be any appropriate variety sufficient to allow air and/or particles to flow through the tubes. Thus the cross-section could be a square, polygon, ellipse or circle. For practical considerations the tubes are preferably of circular cross-section. By varying the inside cross-sectional area of the various tubes and the length of the particle inlet tube 24 the particle flow into the chamber may be regulated. In general the inside diameter of air inlet tube 22 will be about 1 millimeter (mm) to about 2.5 mm (about 0.04 inch [in] to about 0.1 inch), preferably about 1.25 mm.

The size of the inside diameter of the particle inlet tube 24 will be about 0.4 mm to about 0.8 mm. The length of tube 24 will generally be about 4 mm to about 15 mm. The size of the inside diameter of the outlet tube 26 will be about 1.25 mm. The interior volume of chamber 28 will generally be large enough to provide consistent mixing of the particles with the pressurized air to provide a stream of particle-laden gas that can be directed against a surface such as a tooth that can be prepared for further work. The total volume of chamber 28 will be between about 30 ($mm^3$) and about 500 $mm^3$, preferably about 130 $mm^3$. By adjusting the flow of gas, the size of the tubes and chamber, and the particle size, one obtains a flow of particles from the device to be suitable for the desire task. For purposes of dental application, the flow rate of particles is between about 1 grams per minutes (gpm) to about 15 gpm, preferably about 4 to about 6 gpm.

Figure 2:
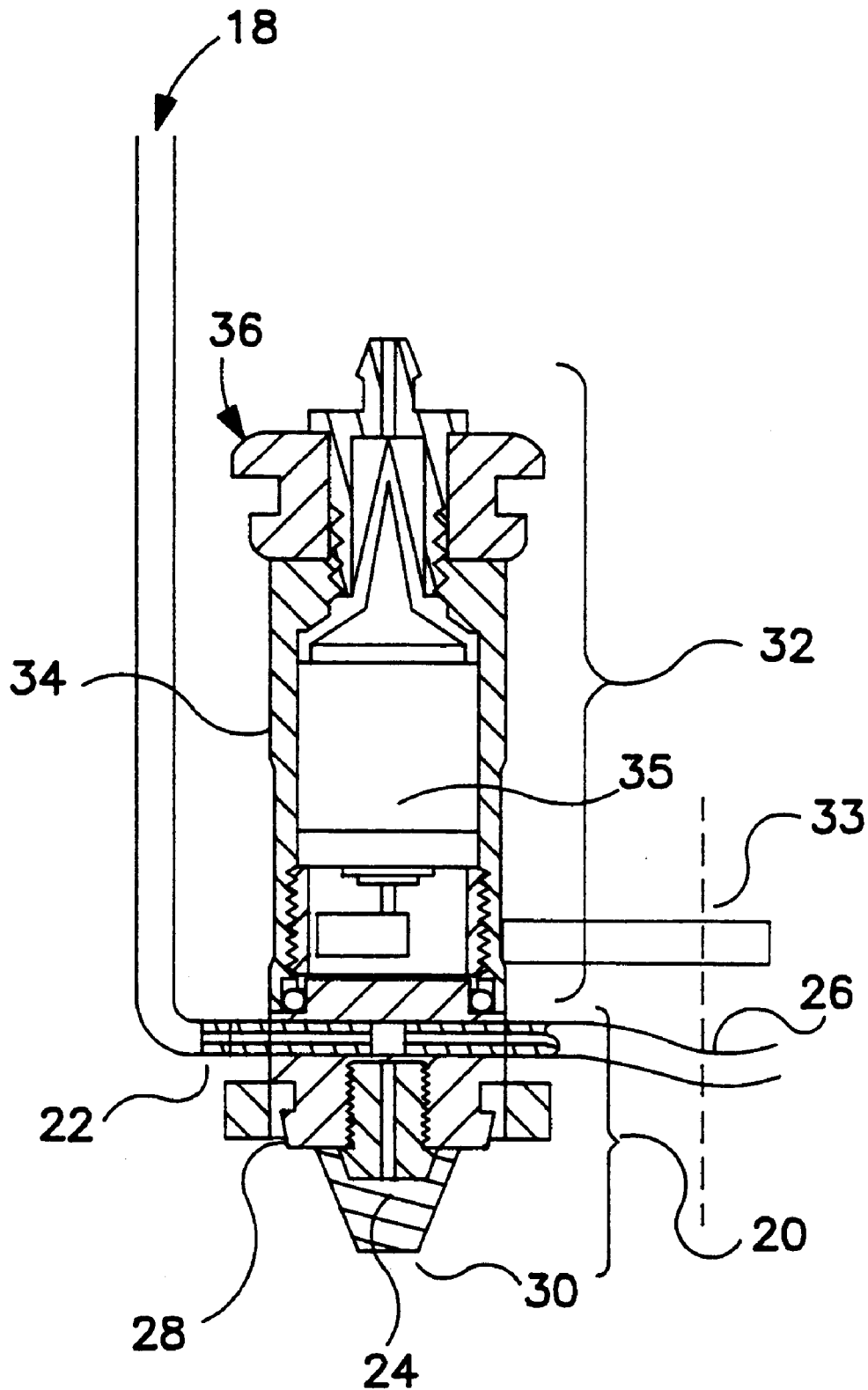
FIG. 2 is a vertical cross-sectional view of a vibrator assembly integrated with a device for producing a pressurized stream of gas and suspended particles.

In FIG. 1 and FIG. 2, the device 20 is shown as being attached to an assembly 32 for producing vibrations within the mass of flowable particles 15. The vibration-producing assembly 32 may be pneumatically or electrically powered but is designed to produce vibrations that are distributed throughout the mass of flowable particles so that as particles 15 are removed from the interior 12 of container 11 though screen 30 and inlet tube 24, other particles relatively uniformly flow downwardly to fill up the void left by the removal of the particles. Preferably the vibrator assembly includes a vibrator motor 35 that produces the vibrations and that may be of any suitable design, but a small permanent magnet motor such as one available through Micro Motors is preferred. The motor is held within a housing 34 that has a cushioned grommet or collar 36 extending around at least a portion of the housing 34. A bracket 37 fits around collar 36 to securely hold the collar and housing and at the same time attach to a tie rod shown as 39 to hold the entire vibrator in place in the interior 12 of container 11. The vibrations created by the assembly prevents the occurrence of a cavity created by the suction around the screen 30, which in turn would prevent the abrasive particles from efficiently entering into the pickup chamber 28, thereby creating sporadic, erratic, and inefficient flow of the air/abrasive mixture.

Such vibrations created by the vibrator assembly are further transmitted through at least one vibration antenna or transmitter 33, which is attached to the vibration-producing assembly 32 at housing 34 and extends radically therefrom. An embodiment of such a vibration transmitter 33, is for it to be located as low as possible in the jar interior 12 and reach out as close to the wall of the jar interior 12 as possible. The vibration transmitter 33 may be any shape such as a straight rod, a flat sheet or in the shape of a triangular "cookie cutter." Preferably, several of these are attached to the vibrator 32 of the pickup body 34 with the outer edge of the vibration transmitter 33 as close to the sidewall 17 of the jar interior 12 as possible.

While the vibrator assembly is shown to be combined with the device for delivering a pressurized stream of gas and suspended abrasive particles, it is to be understood that vibrator assembly in combination with the vibration transmitter is useful alone to maintain the favorable flow of particles under gravity feed in other industries such as the pharmaceutical or food additive industries. For example, if flowable particles are to be gravity fed from a large container into smaller containers or into capsules or a tabletting machine and the gravity flow needs to be uniform, a suitably sized vibrator assembly (including transmitter) can be placed in the large container to, in essence, perform the same role as shown in FIG. 1, namely preventing cavitation as the particles are removed from the bottom of the container, e.g., from outlet 38 if plug 42 were removed. Turning again to FIGS. 1 and 2, the vibration assembly and the device for delivering a pressurized stream of gas and suspended particles are joined together by any suitable means that will allow them to stay together during the production and transmission of the vibrations throughout the mass of particles. For example, the bottom portion of the housing 34 may have a threaded female portion that receives a complementary threaded male portion of the device for producing a pressurized stream of gas and suspended particles. The entire combination is then held in place by bracket 37, which is secured to vertical support 39. When the motor 32 is turned on, the entire combination vibrates as the bracket 37 remains relatively stationary as the cushioned collar 36 flexes with the vibrations.

In the embodiment shown in FIG. 1, the jar 11 has a bottom 40 with sloped internal sides to promote abrasive flow to the pickup chamber 28 and to allow easy removal of all abrasive by the use of the abrasive outlet 38. The embodiment illustrated in FIG. 1 utilizes a plug 42 for control of abrasive removal. For facilitating the adding of more abrasive in jar 11, an abrasive inlet 41 door is provided.

Figure 3:
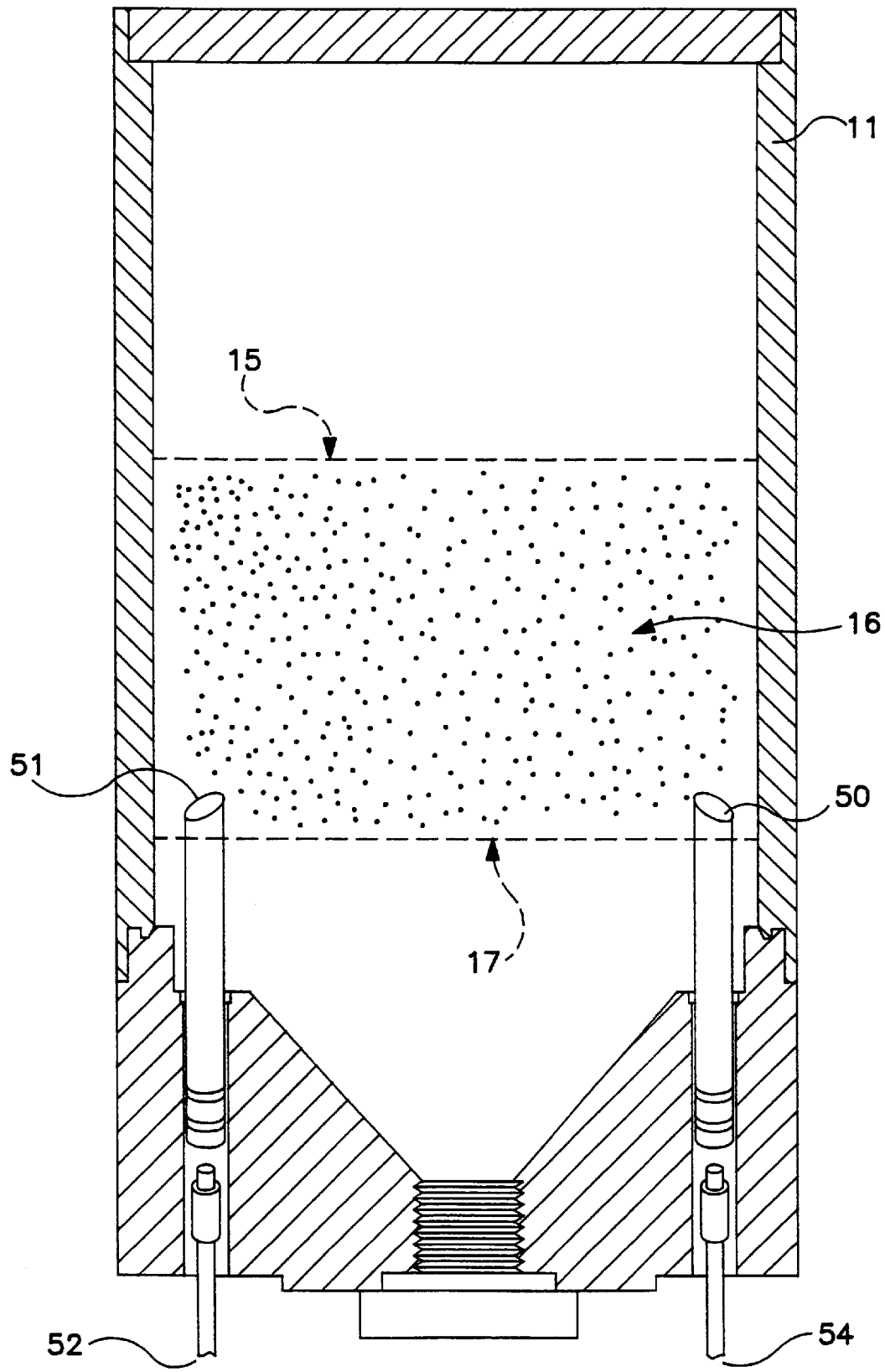
FIG. 3 is a vertical cross-sectional view of a container with an optico-electric level detecting means.

Turning now to another aspect of this invention in FIG. 3 and viewing it in conjunction with FIG. 1, one can see a means for detecting when the upper surface level 15 of the mass of particles 16 drops below a predetermined level 17 in container 11. The upper level 15 of the mass of particles should be monitored continuously to assure that the particle inlet tube 24 is submerged in the particles. One method of determining level 15 is through photo optical detection. Light, for example a bulb or a light emitting diode (LED), is transmitted across the interior of the jar 11 at the desired height for detection. At the same height, the light is detected by a photo diode. If the particles' to upper level 15 is above this desired height, the light will not be observed by the photo diode. As soon as the upper surface level of the particles drops below the photodiode, a circuit is completed to provide a signal, audible or visual, that indicates more particles need to be added to container 11. Another form of photo optical detection is shown in FIG. 3. Here, light is transmitted through transparent rods 50 and 51 with opposing angled faces so that in the manner of a prism, light is reflected at right angles. Transparent rod 51 is associated with LED 52 while rod 50 is associated with photo diode 54, each of which are mounted in removable separate cartridges for easy replacement. Multiple levels of detection are possible by multiple sets of detectors.

While FIGS. 1–3 and 8A–8D provide a more detailed view of the mixing means for combining the pressurized gas with the abrasive particles to form a pressurized stream of gas having particles suspending therein, FIGS. 4–7 provide an overview of a device, or system, for producing a pressurized stream of gas and suspended particles, which is not dependent on having the unique mixing means of FIGS. 1–3 employed in the system. While the container 11 of FIGS. 4–7 is preferably the chamber as shown in FIG. 1, other mixing mean may be usefully employed such as those disclosed in U.S. Pat. Nos. 5,350,299; 3,882,638; 3,852,918; 2,696,049; 4,494,932; 4,708,534; and the like, all of which are incorporated herein by reference.

Thus, another aspect of this invention is a device for producing a pressurized stream of a gas and suspended abrasive particles. The device comprises (a) a source of a pressurized gas; (b) a source of abrasive particles; (c) a mixing means for combining the pressurized gas with said abrasive particles to produce the pressurized stream of gas and suspended particles; (d) an inlet line for the pressurized gas to flow to the mixing means; (e) an outlet line from the mixing means to carry the pressurized stream of gas and suspended particles away from the mixing means; (f) a variable pressure regulator means for controlling the pressure of the gas supplied to the mixing means through the inlet line; (g) a first mixing chamber positioned in the outlet line; (h) a source of regulated pressurized gas leading to the first mixing chamber to provide dilution of the pressurized stream of gas and suspended particles; (i) a nozzle means downstream of the first mixing chamber for delivering the pressurized stream of gas and suspended particles to a surface; and (j) a first valve located intermediate of the mixing means and nozzle means for regulating the flow of the pressurized stream of gas and suspended particles to the nozzle means so that the pressurized stream of gas and suspended particles may be directed against a surface to be abraded.

Figure 4:
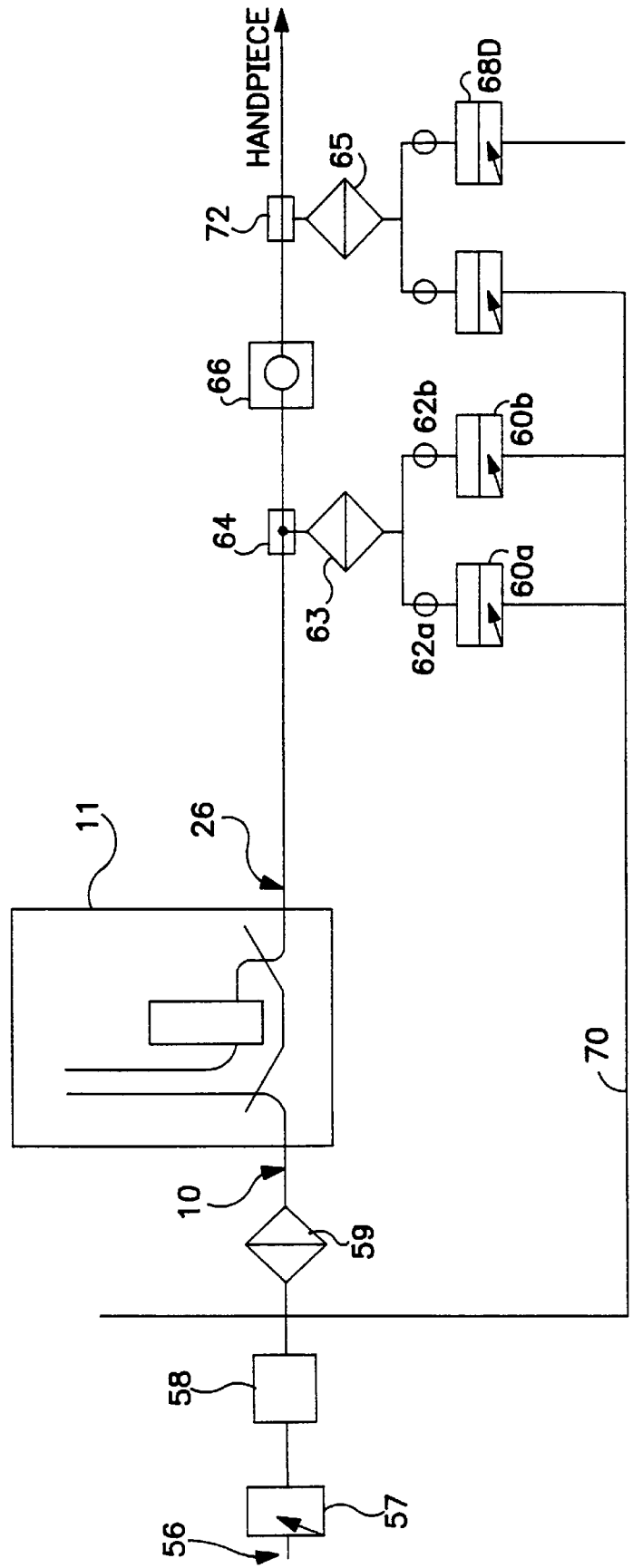
FIG. 4 is a schematic diagram of a dental air abrasive system in accordance with this invention.

Turning now to FIG. 4, one can see an overall scheme of an air abrasive system that is useful for a dentist to clean the surface of a tooth in preparation for further work on the tooth surface. For example, the clinical applications of the system include: tooth surface preparation prior to fissure sealing; preventive resin preparations; any pit or fissure preparation; cervical (Class V) preparations; Class III preparations; removal of old composite resins and tunnel type preparations; desensitization of cervical dentin; cleaning and dentin sealing of crown preparations prior to cementation; endodontic access (especially through a hot tooth and through porcelain); air abrading fractured porcelain and exposed metal for porcelain repair; air abrading orthodontic bands, "Maryland Bridge" type retainers, stainless steel crowns and the interior of crowns and onlays to improve wetting during cementation; and placing small undercuts in cervical erosions to be restored without further preparation. Preferably, the container 11 corresponds to that shown in FIGS. 1, 2 and 3, with few of the details of FIGS. 1 or 2 included in FIG. 4. For purposes of this discussion, the references to the numbers of FIG. 2 will be the same for FIG. 4.

FIG. 4 illustrates a preferred embodiment of the system that allows the user to dilute the gas particle mixture from outlet tube 26. Pressurized gas from a source such as a compressor flows through the inlet air conduit 56 through a variable pressure regulator means, shown here as solenoid valve 57 and pressure regulator 58. The pressurized gas then flows through an optional filter 59, through and into mixing means, shown as jar 11, where the pressurized air is mixed with abrasive particles, preferably in accordance with the above discussion. The gas/particles mixture then flows through the outlet line 26 and into a first mixing chamber 64. The gas/particles stream that flows from the jar 11 can be diluted with additional gas for applications that require less abrasive for reduced cutting action. This dilution can be accomplished by injecting fluid such as air into the outlet tube 26 at first mixing chamber 64. Pressurized gas from the line connecting pressure regulator 58 and filter 59 flows through the dilution conduit 70 and into a single or multiple number of solenoid valves, shown as 60a and 60b, connected to pre-set flow restrictors, such as needle valves 62a and 62b. The pressurized air then goes through optional filter 63 and is mixed with the air/abrasive mixture in the mixing chamber 64. The dilution may also be accomplished by using a single or multiple variable valve connected to the mixing chamber 64 in the outlet tube 26. The flow downstream of mixing chamber 64 is controlled by a valve (e.g. a pinch valve) located intermediate of the jar 11 and the nozzle means (or handpiece). By closing the pinch valve 66, and opening a valve connected to dilution conduit 70 downstream of pinch valve 66 will allow an "air only" mode in which only pressurized air will flow through junction 72 and to the hand piece. It is desirable to have the gas/particles stream stopped immediately when the pinch valve 66 is closed. However, whenever a reserve of air pressure is in the outlet tube 26, it can cause delayed shutoff. This problem can be solved by opening the dump valve 68 just before or simultaneously with closing pinch valve 66 to more rapidly vent residual pressure.

It is preferable to regulate the pressure of the gas flowing to mixing means 11 by employing pulsed-duty cycle control mechanism such as a solenoid valve in combination with a transducer as discussed hereinafter. If the variable pressure regulator means uses a pulsed-duty cycle, there may be no need for the downstream dilution at 64 or 72. Thus, another aspect of the invention is a device for producing a pressurized stream of a gas and suspended abrasive particles, which device comprises (a) a source of a pressurized gas;
(b) a source of abrasive particles;
(c) a mixing means for combining the pressurized gas with said abrasive particles to produce the pressurized stream of gas and suspended particles;
(d) an inlet line for the pressurized gas to flow to the mixing means;
(e) an outlet line from the mixing means to carry the pressurized stream of gas and suspended particles away from the mixing means;
(f) a variable, pulsed-duty pressure regulator means for controlling the pressure of the gas supplied to the mixing means through the inlet line;
(g) a nozzle means downstream of the mixing means for delivering the pressurized stream of gas and suspended particles to a surface; and
(h) a first valve located intermediate of the mixing means and nozzle means for regulating the flow of the pressurized stream of gas and suspended particles to the nozzle means so that the pressurized stream of gas and suspended particles may be directed against a surface to be abraded.

Alternatively, instead of the device or system having a variable pressure regulator means upstream of the mixing means 11, a regulator providing a constant pressure may be employed. In that case, however, it is preferred to employ a source of regulated, pressurized air (preferably using a pulsed-duty cycle) to feed a mixing chamber 64 in line 26 to dilute the air/abrasive stream as needed for the job at hand. Thus, another aspect of this invention is a device for producing a pressurized stream of a gas and suspended abrasive particles, which device comprises (a) a source of a pressurized gas;
(b) a source of abrasive particles;
(c) a mixing means for combining the pressurized gas with said abrasive particles to produce the pressurized stream of gas and suspended particles;
(d) an inlet line for the pressurized gas to flow to the mixing means;
(e) an outlet line from the mixing means to carry the pressurized stream of gas and suspended particles away from the mixing means;
(f) a pressure regulator means for providing a constant pressure of the gas supplied to the mixing means through the inlet line;
(g) a first mixing chamber positioned in the outlet line;
(h) a source of pressurized gas having the pressure regulated by a pulsed-duty cycle regulator and leading to the first mixing chamber to provide dilution of the pressurized stream of gas and suspended particles;
(i) a nozzle means downstream of the first mixing chamber for delivering the pressurized stream of gas and suspended particles to a surface; and
(j) a first valve located intermediate of the mixing means and nozzle means for regulating the flow of the pressurized stream of gas and suspended particles to the nozzle means so that the pressurized stream of gas and suspended particles may be directed against a surface to be abraded.

Figure 5:
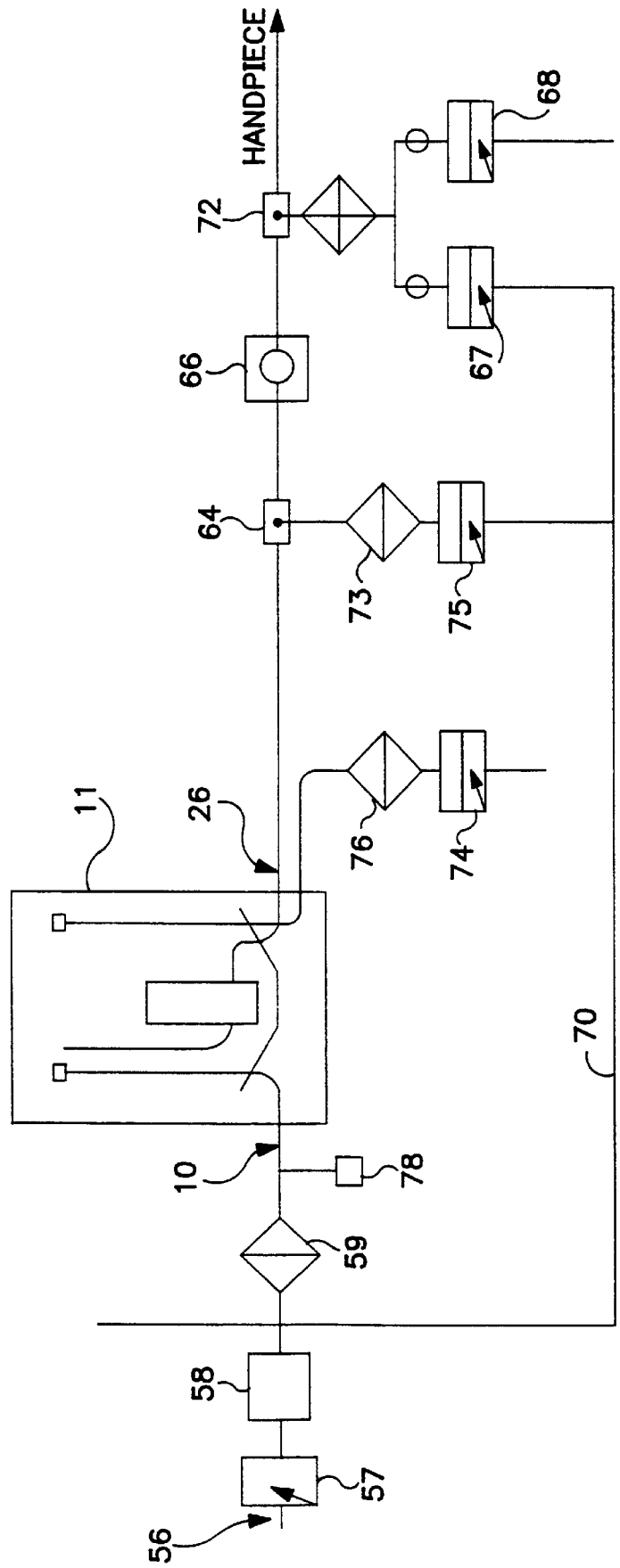
FIG. 5 is an alternative schematic design for a dental air abrasive system in accordance with this invention.

On a regular basis, it may be necessary to depressurize the jar 11 in order to refill with abrasive particles 15 or to remove the abrasive particles 15. It is also necessary to be able to reduce the pressure in the jar 11 when a lower pressure is desired by the operator. FIG. 5 illustrates an embodiment which accommodates depressurization and reduction of pressure. Solenoid valve 74 can be opened and allowed to vent air until ambient pressure or the desired reduced pressure is reached. A filter 76 prevents particles 15 from flowing into the solenoid valve 74. A pressure detector 78, shown as located at the air inlet line 10, such as a gauge or transducer, is used to detect the container 11 pressure. Should a particle of abrasive or a foreign matter become wedged in the interior of the pickup tube 24 (as shown in FIG. 1), it will necessary to clear it to restore the powder flow. This clearance can be accomplished by a backward flow of air into the pickup chamber 28, at FIG. 1. To pressurize the pickup chamber 28 and expel the particle, the solenoid valve 74 can be opened for a short duration, typically one to two seconds, and simultaneously open the solenoid valve 75 while closing pinch valve 66.

Figure 6:
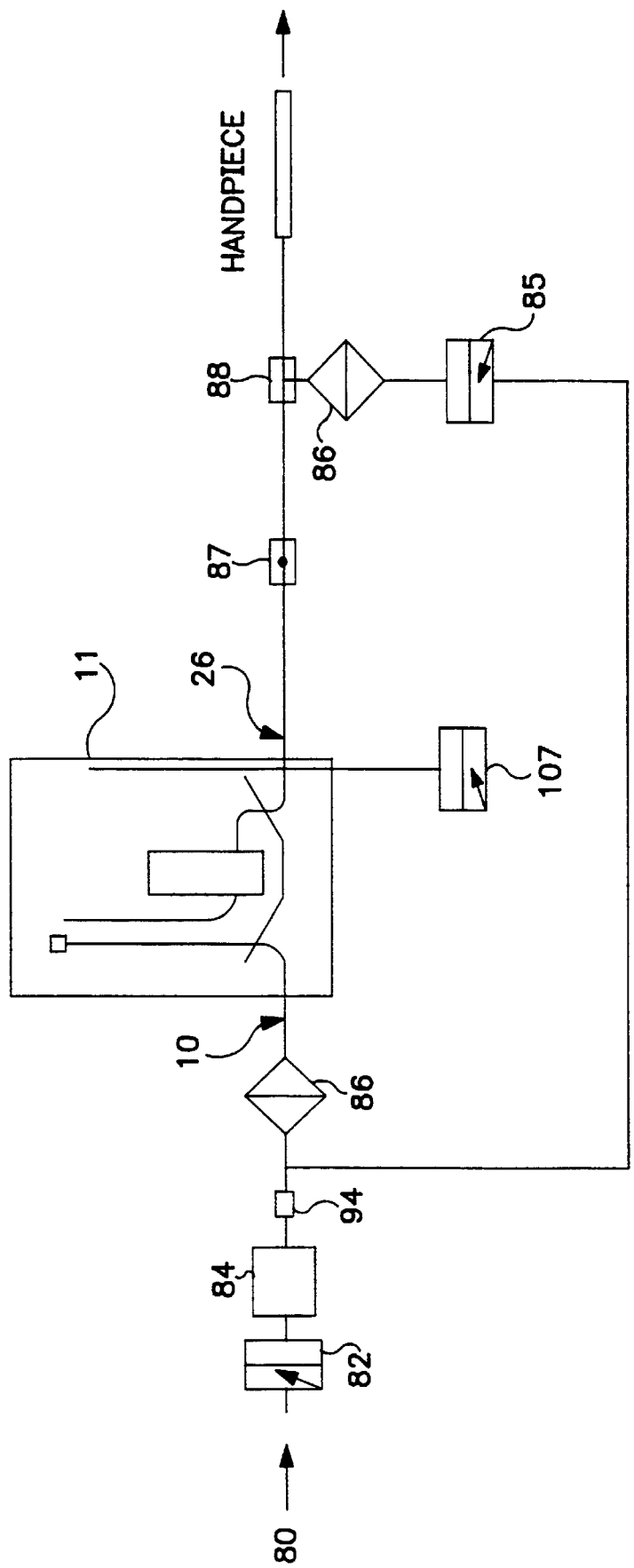
FIG. 6 is an alternative schematic design for a dental air abrasive system in accordance with this invention.

Another embodiment is illustrated in FIG.6. The compressed gas flows from the source 80 and flows into the solenoid valve 82. The solenoid valve 82 controls both air delivery and air pressure by pulsed-duty cycle control. The system functions normally at 3–10 cycles/second and 0–100% duty cycle. Pressure is measured by a transducer 94, and the duty cycle is varied to keep pressure at a desired level. If the desired pressure increases, valve 107 can be opened until the pressure has decreased to the desired level, as reported by transducer 94. The duty cycle of valve 82 can be varied as much as desired to achieve any pressure not exceeding the input pressure, within the range of accuracy of the transducer 94. The air then flows into an optional holding tank 84 which evens out pulses of air. The size of holding tank 84 varies inversely with the size of the container 11, whose volume also serves to even out pulses of air, and with the frequency of operation of the solenoid valve 82. An optional filter 86 prevents backward flow of particles from the container 11, while the container 11 accurately mixes compressed air with abrasive as described hereinbefore. The pinch valve 87 controls the flow of the air/abrasive stream. The solenoid valve 85 which controls the air delivery to air mixture chamber 88, is also pulsed. The solenoid valve 85 also functions at 3–10 cycles per second and 0–100% duty cycle. The injected air from solenoid valve 85 mixes with the gas/particle stream in the mixing chamber 88 where the injected air dilutes the gas/particle mixture to the desired mixture. Valve 85's duty cycle can be varied widely to achieve a theoretically infinite number of possible air/abrasive mixture settings. The diluted stream of air/abrasive then flows to the hand-piece.

Figure 7:
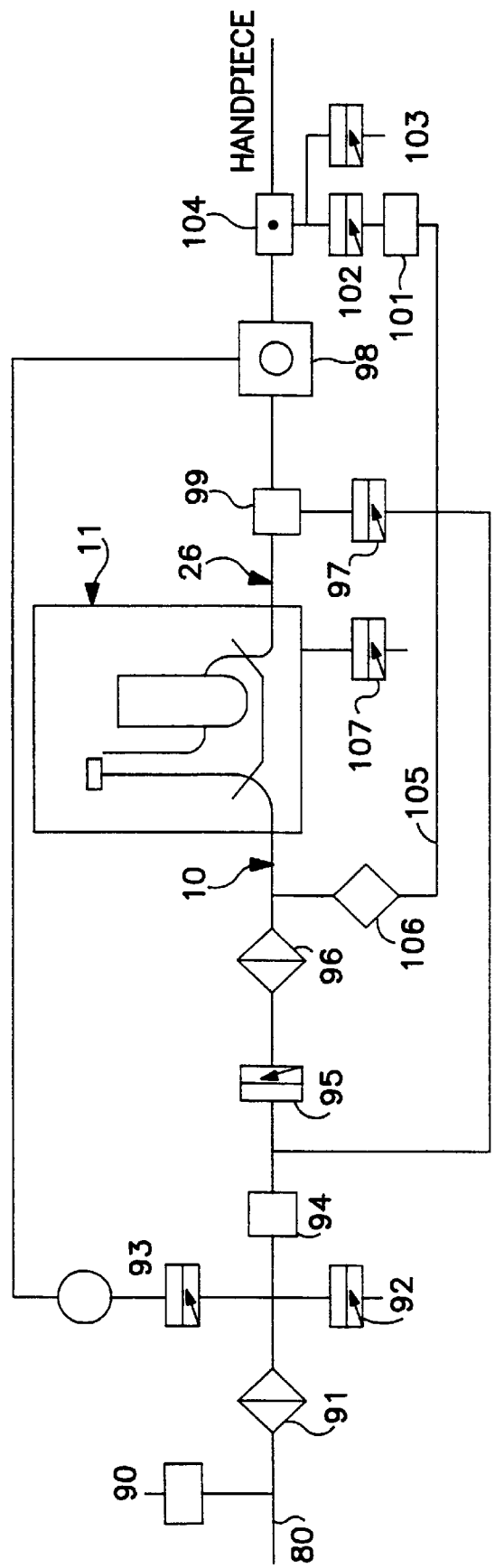
FIG. 7 is an alternative schematic diagram for an air abrasive system in accordance with this invention.

FIG. 7 shows a slightly modified arrangement of another embodiment of a system for providing an air/abrasive stream to prepare the surface of teeth in accordance with this invention. Here, the air line designated as 80 is equipped with a pressure relief valve designated as 90 which may be rated at a particular pressure rating such as 150 psi. This provides a relief mechanism and protection to the patient and the doctor should the pressure in the line exceed such a level. The air flows through an optional filter and oil water trap 91 to ensure that there is no particulate matter, no condensed oil or condensed water that gets into the line. Solenoid valve 93 is connected to pinch valve 98 to regulate when the pinch valve is opened or closed. Solenoid valve 92 can be used to drain any water that may condense from the line 80. This particular design of the system shown in FIG. 7 is dependent upon transducers, devices that convert input energy of air pressure to an output energy (electrical energy) to help regulate the system. A transducer, shown as 94, senses the pressure that is in the line. If the pressure goes above a certain level, a signal is sent to certain of the valves to close. If the pressure is below a certain level, it sends a signal to open. The air then continues to flow through the air line to solenoid valve 95 and through an optional desiccant and filter designated as 96. The container 11 is situated in the line and preferably operates consistent with the discussion of FIGS. 1, 2 and 3 as discussed hereinbefore. The container 11 has an inlet line 10 and an outlet line 26. The abrasive laden air stream exiting from container 12 through exit line 26 can be diluted in mixing chamber 104 by additional air which goes through line 105 through solenoid valve 102. Optionally, additional or alternative dilution may take place at mixing chamber 98. The flow of the optionally diluted abrasive air stream goes through pinch valve 98 to chamber 104 where it can be mixed with additional air or simply go to the handpiece. If mixed with additional air, the air comes from a take-off point from entry line 10 through line 105 to a second transducer 101 and a solenoid valve 102. An air bleed solenoid valve 103 is attached just prior to the chamber 104 for rapid reduction of pressure when desired. The transducers 94 and 101 monitor the pressure level in the line and control the opening and closing of the valves to operate the system at between 0–100%. For example referring to 101 and 102, at 0% solenoid valve would be closed and no dilution would take place, while at 100% solenoid valve would be open fully for maximum dilution at 104. The pressure values at which the signal is sent to turn the system off or on may be preset at, for example, 80 psi, 100 psi, or 120 psi, depending on the desired pressure level. If the transducer 94 senses the pressure is beyond the desired level, the solenoid valve 107 will be opened to reduce the pressure in the system and bleed off pressure from the container 11. By using this particular setup for the system, the user is allowed to easily clean the system in case it gets plugged, for example, by inadvertently having a particle clog the inlet line 24, as shown in FIG. 1. To backflush the jar and clean such a blockage of the line, the user would simply close solenoid valve 95 while at the same time opening solenoid valve 97, while closing pinch valve 98, allowing air to flow through line 100 and solenoid valve 97 through junction 99 back through line 26 to backflush the system. At the same time that solenoid valve 97 is open and solenoid valve 95 is closed, solenoid valves 102 and 103 are both open to allow for pressure relief of the system. The presence of filter 106 in line 105 prevents any particles from getting to transducer 101 or solenoid valves 102 or 103.

By the arrangement shown in FIG. 7, it is easy to dilute the air/abrasive stream coming out of the outlet line 26. Such dilution can be done at exit block 104, if desired. In general, the system is activated by pressing a footswitch, not shown, which will open valve 95 to allow the flow of air through line 80 to entry line 10, while solenoid valve 107 is closed. The air flows into container 11, picks up the abrasive material, preferably as discussed previously, and exits through outlet line 26. Solenoid valve 93 operates to open the pinch valve 98, allowing the air/abrasive stream to then flow to the exit block 104 where it may be further diluted before going to the handpiece, i.e. nozzle means. When the user then takes his or her foot off the footpiece, solenoid valve 107 is opened to release the pressure and more quickly cease the flow of the air/abrasive mixture. Solenoid valve 95 will operate in conjunction with transducer 94 with the transducer sensing the pressure level and sending the appropriate message to open or close valves should the pressure increase or decrease above or below a certain level. The flow rate of the abrasive material, as well as the pressure of the system, can then be modified as required by the user. The modification may be done by the user by using a table to determine what flow rate and what pressure level is desired for which operation. On the other hand, the desired flow rate and pressure may be regulated by a computer that sets the desired pressures.

Figure 8C:
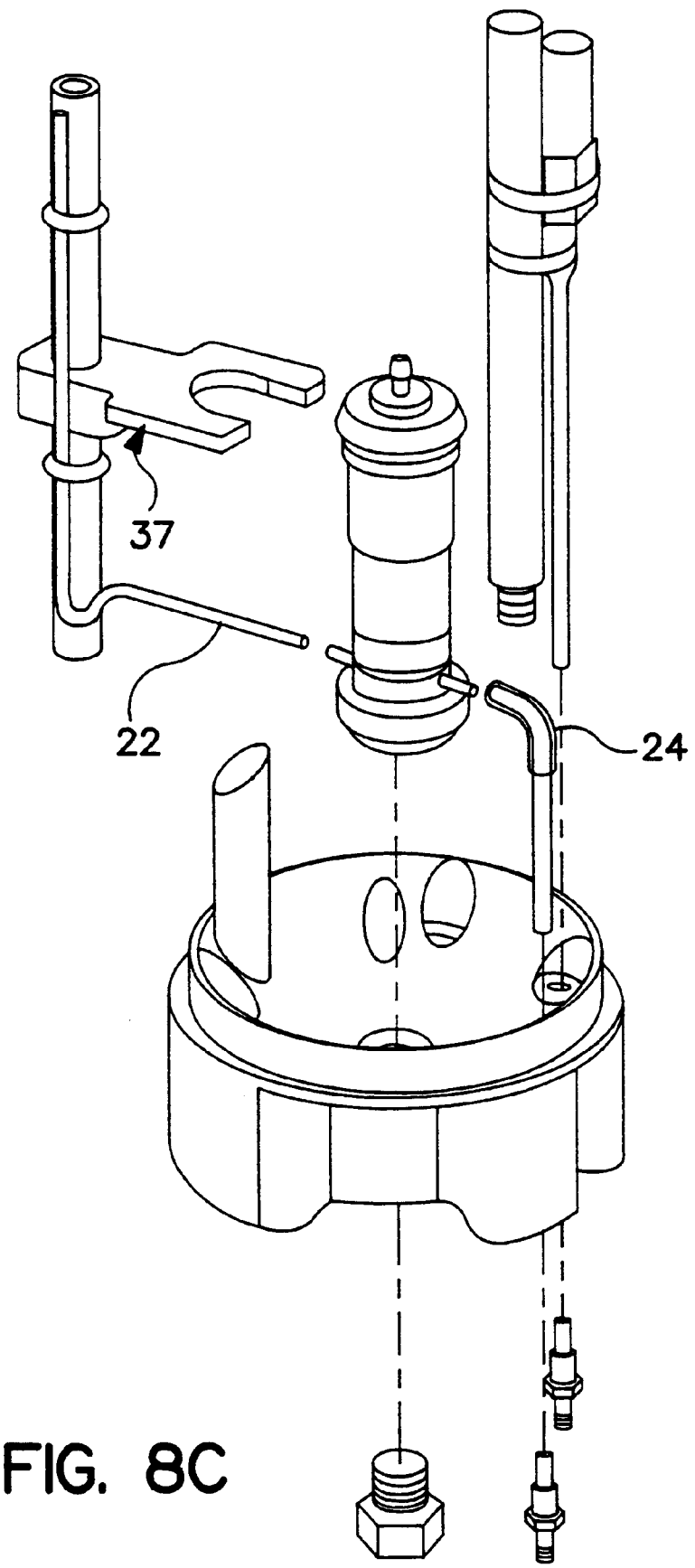
Figure 8D:
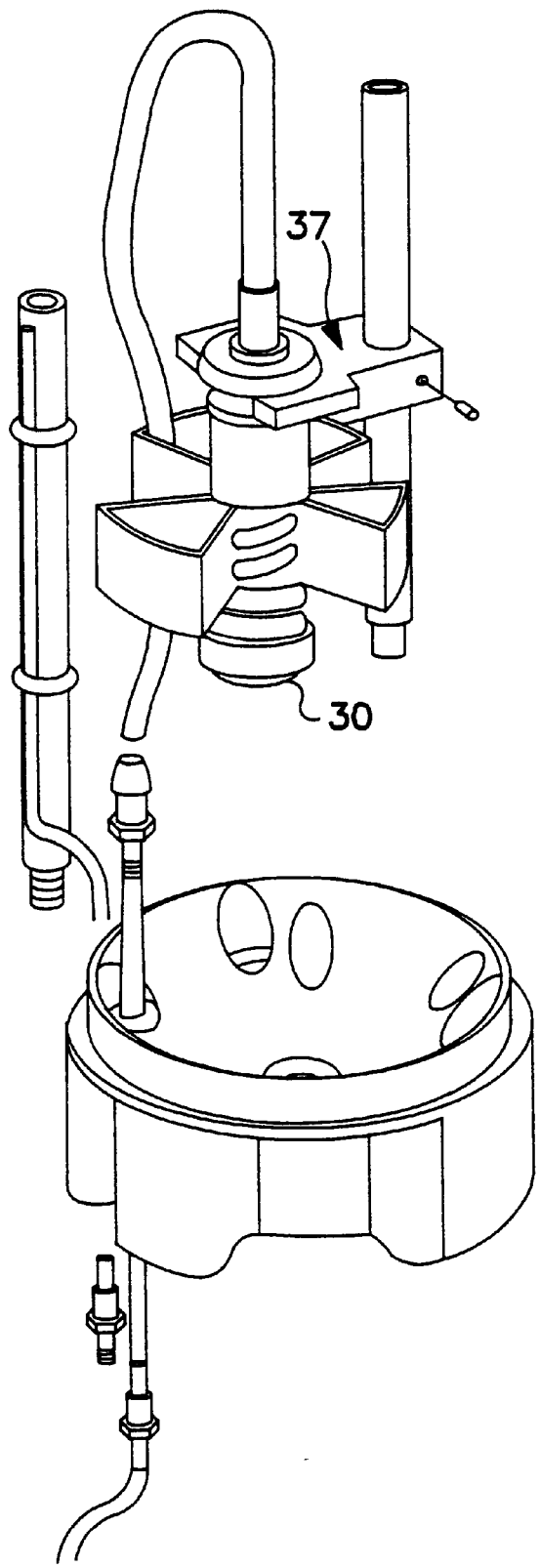

A further detailed view of the container vibrator assembly and device for producing a stream of pressurized gas air particles is shown in FIGS. 8A, 8B, 8C and 8D. Here you can more clearly see as an exploded view the various components of the system. For example, in FIG. 8A one can see how the vibrator assembly and the vibration transmitters or antennae 33 are designed in the "cookie cutter" design. This is a triangular design shown extending from the periphery of the vibrator assembly housing. One can see also the detail of the container having top 40, side wall 17 and bottom wall 40. FIG. 8B shows the LED 52 and the screw 53 which is used to attach it and its components to the bottom wall 40 of the container 11. Similarly, the photodiode of 54 is attached using screw 55. Other aspects of the details of the invention can be seen in FIGS. 8C and 8D, where it is seen where bracket 37 fits into collar or grommet 36 to hold the internal vibrator assembly in place. Further, one can see air inlet tube 22 and the outlet tube 24 along with screen 30 for the abrasive pickup assembly 20.

The invention now being fully described, it will be apparent to one of ordinary skill in the art that many changes and modifications can be made thereto without departing from the spirit or scope of the appended claims.

What is claimed is:

1. A device for producing a pressurized stream of a gas and suspended abrasive particles, which device comprises (a) a source of a pressurized gas;
    (b) a source of abrasive particles;
    (c) a mixing means for combining the pressurized gas with said abrasive particles to produce the pressurized stream of gas and suspended particles;

(d) an inlet line for the pressurized gas to flow to the mixing means;

(e) an outlet line from the mixing means to carry the pressurized stream of gas and suspended particles away from the mixing means;

(f) a variable pressure regulator means for controlling the pressure of the gas supplied to the mixing means through the inlet line;

(g) a first mixing chamber positioned in the outlet line;

(h) a source of regulated pressurized gas leading to the first mixing chamber to provide dilution of the pressurized stream of gas and suspended particles;

(i) a nozzle means downstream of the first mixing chamber for delivering the pressurized stream of gas and suspended particles to a surface; and (j) a first valve located intermediate of the mixing means and nozzle means for regulating the flow of the pressurized stream of gas and suspended particles to the nozzle means so that the pressurized stream of gas and suspended particles may be directed against a surface to be abraded.

2. The device of claim 1 wherein the device includes a second mixing chamber downstream of the first mixing chamber and intermediate the first valve and the nozzle means and a source of regulated, pressurized air leading to the second mixing chamber to provide a stream of particle free air to the second mixing chamber.

3. The device of claim 2 wherein a pressure relief valve is associated with the second mixing chamber to provide pressure relief to the outlet line.

4. The device of claim 1 wherein the variable pressure regulator means is a solenoid valve that controls both the air delivery and air pressure by pulse-duty cycle control.

5. The device of claim 4 wherein the solenoid valve operates in conjunction with a transducer located down stream from the solenoid valve, which transducer measures the pressure in the inlet line and the duty-cycle varies to keep the pressure at a desired level.

6. The device of claim 5 wherein a holding tank is located down stream of the transducer intermediate of the mixing means, wherein the holding tank evens out the pulses of air to maintain a regular pressure going to the mixing means.

7. The device of claim 1 wherein said first valve is located intermediate of the mixing chamber and the nozzle means.

8. A device for producing a pressurized stream of a gas and suspended abrasive particles, which device comprises (a) a source of a pressurized gas;

(b) a source of abrasive particles;

(c) a mixing means for combining the pressurized gas with said abrasive particles to produce the pressurized stream of gas and suspended particles;

(d) an inlet line for the pressurized gas to flow to the mixing means;

(e) an outlet line from the mixing means to carry the pressurized stream of gas and suspended particles away from the mixing means;

(f) a variable, pulsed-duty pressure regulator means for controlling the pressure of the gas supplied to the mixing means through the inlet line;

(g) a nozzle means downstream of the mixing means for delivering the pressurized stream of gas and suspended particles to a surface; and (h) a first valve located intermediate of the mixing means and nozzle means for regulating the flow of the pressurized stream of gas and suspended particles to the nozzle means so that when the first valve is open the pressurized stream of gas and suspended particles may be directed against a surface to be abraded.

9. A device for producing a pressurized stream of a gas and suspended abrasive particles, which device comprises (a) a source of a pressurized gas;

(b) a source of abrasive particles;

(c) a mixing means for combining the pressurized gas with said abrasive particles to produce the pressurized stream of gas and suspended particles;

(d) an inlet line for the pressurized gas to flow to the mixing means;

(e) an outlet line from the mixing means to carry the pressurized stream of gas and suspended particles away from the mixing means;

(f) a pressure regulator means for providing a constant pressure of the gas supplied to the mixing means through the inlet line;

(g) a first mixing chamber positioned in the outlet line;

(h) a source of pressurized gas having the pressure regulated by a pulsed-duty cycle regulator and leading to the first mixing chamber to provide dilution of the pressurized stream of gas and suspended particles;

(i) a nozzle means downstream of the first mixing chamber for delivering the pressurized stream of gas and suspended particles to a surface; and (j) a first valve located intermediate of the mixing means and nozzle means for regulating the flow of the pressurized stream of gas and suspended particles to the nozzle means so that the pressurized stream of gas and suspended particles may be directed against a surface to be abraded.

10. A device for producing a pressurized stream of a gas and suspended abrasive particles, which device comprises (a) a source of a pressurized gas;

(b) a source of abrasive particles;

(c) a mixing means for combining the pressurized gas with said abrasive particles to produce the pressurized stream of gas and suspended particles;

(d) an inlet line for the pressurized gas to flow to the mixing means;

(e) an outlet line from the mixing means to carry the pressurized stream of gas and suspended particles away from the mixing means;

(f) a variable pressure regulator means for controlling the pressure of the gas supplied to the mixing means through the inlet line;

(g) a first mixing chamber positions in the outlet line;

(h) a source of having the pressure regulated by a pulsed-duty cycle regulator and pressurized gas leading to the first mixing chamber to provide dilution of the pressurized stream of gas and suspended particles;

(i) a nozzle means downstream of the first mixing chamber for delivering the pressurized stream of gas and suspended particles to a surface; and (j) a first valve located intermediate of the mixing means and nozzle means for regulating the flow of the pressurized stream of gas and suspended particles to the nozzle means so that the pressurized stream of gas and suspended particles may be directed against a surface to be abraded.

* * * * *